United States Patent [19]

Madsen et al.

[11] Patent Number: 5,189,016
[45] Date of Patent: Feb. 23, 1993

[54] NUTRIENT COMPOSITIONS CONTAINING PEPTIDES AND METHOD FOR ADMINISTERING THE SAME

[75] Inventors: David C. Madsen, Libertyville; W. Bruce Rowe, Evanston, both of Ill.

[73] Assignee: Clintec Nutrition Co., Deerfield, Ill.

[21] Appl. No.: 525,861

[22] Filed: May 18, 1990

[51] Int. Cl.$^5$ .................... A61K 37/00; A61K 31/70
[52] U.S. Cl. ......................................... 514/2; 514/23
[58] Field of Search ................... 514/561, 566, 2, 23

[56] References Cited

U.S. PATENT DOCUMENTS

| | | | |
|---|---|---|---|
| 4,340,592 | 7/1982 | Adibi | 514/561 |
| 4,636,490 | 7/1987 | Martinez et al. | 514/15 |
| 4,758,675 | 7/1988 | Hansen et al. | 514/15 |
| 4,987,123 | 1/1991 | Masaki et al. | 514/561 |

FOREIGN PATENT DOCUMENTS

| | | |
|---|---|---|
| 0087751 | 5/1985 | European Pat. Off. |
| 0087750 | 6/1985 | European Pat. Off. |
| 0182356 | 5/1986 | European Pat. Off. |
| 0346501 | 12/1989 | European Pat. Off. |
| 0347890 | 12/1989 | European Pat. Off. |
| 3206810C2 | 12/1983 | Fed. Rep. of Germany |
| 3206784C2 | 5/1985 | Fed. Rep. of Germany |

OTHER PUBLICATIONS

Burns et al, Arginine: An Indispensable Amino Acid for Mature Dogs, J. Nutr. 111: 1020-1024, 1981.
Chyun et al, Improvement of Nitrogen Retention by Arginine and Glycine Supplementation and Its Relation to Collagen Synthesis in Traumatixed Mature and Aged Rats, J. Nutr. 114: 1697-1704, 1984.
Czarnecki et al, Urea Cycle Function in the Dog with Emphasis on the Role of Arginine, J. Nutr. 114: 581-590, 1984.
Fahey et al, Effect of L-Arginine on Elevated Blood Ammonia Levels in Man, American Journal of Medicine, 860-869 (1957).
Brusilow, Arginine, an Indispensable Amino Acid for Patients with Inborn Errors of Urea Synthesis, J. Clin. Invest., vol. 74, Dec. 1984, 2144-2148.
Rudman et al, Hypotyrosinemia, Hypocystinemia, and Failure to Retain Nitrogen During Total Parenteral Nutrition of Cirrhotic Patients, Gastroenterology 1981:81:1025-35.
Rose, The Amino Acid Requirements of Adult Man, Nutrition Abstracts and Reviews, vol. 27, No. 3, Jul. 1957, 631-647.
Laidlaw et al, Newer Concepts of the Indispensable Amino Acids, Am J. Clin Nutr 1987; 46:593-605.
du Ruisseau et al, Studies on the Metabolism of Amino Acids and Related Compounds in Vivo, IV, Blood Ammonia and Urea Levels Following Intraperitoneal Administration of Amino Acids and . . . , Archives of Biochemistry and Biophysics 64, 355-367 (1956).
Brown et al, Transiently Reduced Activity of Carbamyl Phosphate Synthetase and Ornithine Transcarbamylase in Liver of Children with Reye's Syndrome, N. Engl J. Med, vol. 294, No. 16, 861-867, 1976.
Barbul et al, Immunostimulatory Effects of Arginine in Normal and Injured Rats, Journal of Surgical Research 29, 228-235 (1980).
Barbul et al, Arginine: Biochemistry, Physiology, and Therapeutic Implications, J. of Parenteral and Enteral Nutrition, vol. 10, No. 2, 1986, 227-238.
Anderson et al, Lysine and Arginine Requirements of the Domestic Cat, 1368-1372 (1979).
Abel et al, Improved Survival from Acute Renal Failure After Treatment With Intravenous Essential L-Amino Acids and Glucose. The New England Journal of Medicine, vol. 288, No. 14, Apr. 5, 1973, 695-699.
Anderson et al, Effects of Excess Arginine with and Without Supplemental Lysine on Performance, Plasma Amino Acid Concentrations and Nitrogen Balance of Young Swine, Journal of Animal Science, vol. 58, No 2, 1984 369-377.
Adibi, Intravenous Use of Glutamine in Peptide Form: Clinical Applications of Old and New Observations, Metabolism, vol. 38, No. 8 (1989), pp. 89-92.
Adibi et al, Influence of Molecular Structure on Half-Life and Hydrolysis of Dipeptides in Plasma: Importance of Glycine as N-Terminal Amino Acid Residue, Metabolism, Col. 35, No. 9 (1986), 830-836.
Gopalakrishna et al, Effect of Growth & Differentiation on Distribution of Arginase & Arginine in Rat Tissues, Indian Journal of Biochemistry & Biophysics, vol. 16, Apr. 1979, 66-68.
De Aloysio et al, The Clinical Use of Arginine Aspartate in Male Infertility, Acta Eut Fertil 1982; 13: 133-67.
Deshmukh et al, Arginine Requirement and Ammonia Toxicity in Ferrets, J. Nutr. 113: 1983, 1664-1667.
Carey et al, An Arginine-Deficient Diet in Humans Does Not Evoke Hyperammonemia or Orotic Aciduria, American Institute of Nutrition (1987) 1734-1739.

(List continued on next page.)

Primary Examiner—Frederick E. Waddell
Assistant Examiner—Raymond J. Henley, III
Attorney, Agent, or Firm—Hill, Steadman & Simpson

[57] ABSTRACT

The present invention relates to nutrient compositions containing dipeptides and methods for administering the same. In particular, according to the present invention, a nutrient composition comprising an aqueous solution having at least one dipeptide with an N-terminal amino acid selected from the class consisting of glutamine, asparagine, tyrosine, tryptophan, and asparagine is provided. Glutamine (4.8 grams/100 ml at 30° C.), asparagine (3.5 grams/100 mL at 28° C.), tyrosine (0.45 grams/100 mL at 25° C.) and tryptophan (11.4 grams/100 mL at 25° C.) and arginine (15.0 grams/100 mL at 21° C.) are all less soluble in water than glycine (25 grams/100 mL at 25° C.). The C-terminal amino acid is selected from the group consisting of alanine, glycine, tryptophan, arginine, proline and serine. The nutritional solutions contain from about 0.1 to 25.0 percent by weight of oligopeptides, preferably about 0.5 to 5.0 percent by weight.

7 Claims, No Drawings

OTHER PUBLICATIONS

Brusilow et al, Arginine Therapy of Argininosuccinase Deficiency, The Lancet, Jan. 29, 1979, 124–127.

Arginine as an Essential Amino Acid in Children With Argininosuccinase Deficiency, Nutrition Reviews, vol. 37, No. 4, 1979, 112–113.

Elsair et al, E-fect of Arginine Chlorhydrate on Nitrogen Balance During the Three Days Following Routine Surgery in Man, Biomedicine, 1978, 29, 312–317.

Ueda et al, Kyotorphin (Tyrosine-Arginine) Synthetase in Rat Brain Synaptosomes, The Journal of Biological Chemistry, vol. 262, No. 17, 1987, 8165–8173.

Takagi et al, A Novel Analgesic Dipeptide from Bovine Brain is a Possible Met-Enkephalin Releaser, Nature, vol. 282, 1979, 410–412.

Ueda et al, A Met-Enkephalin Releaser (Kyotorphin)-Induced Release of Plasma Membrane-bound $Ca^{2+}$ From Rat Brain Synaptosomes, Brain Research 419 (1987) 197–200.

Furst et al, Stress-Induced Intracellular Glutamine Depletion, Contr. Infusion Ther. Clin. Nutr., vol. 27, (1987), 117–136.

Auspen, 16th Annual Scientific Meeting, 18–19, Tyrosine-Arginine (Tyr-Arg): A Soluble Form of Tyrosine (1986).

Stehle, P. et al., "Effect of Parenteral Glutamine Peptide Supplements on Muscle Glutamine Loss and Nitrogen Balance After Major Surgery," 1 Lancet 231 (Feb. 1989).

Steininger et al., "Infusion of Dipeptides as Nutritional Substrates for Glutamine, Tyrosine, and Branched-Chain Amino Acids in Patients with Acute Pancreatitis, "Meta. 78 (Aug. 1989).

Albers, S. et al. "Availability of Amino Acids Supplied Intravenously in Healthy Man as Synthetic Dipeptides: Kinetic Evaluation of L-alanyl-L-glutamine and glycyl-L-tyrosine", 75 Clin. Sci. 463 (1988).

Brandt, et al., "Parenteral Nitrition with an Amino Acid Solution Containing a Mixture of Dipeptides, Evidence for Efficient Utilization of Dipeptides in Man," Contr. Infusion Ther. Clin. Nutr. 17, pp. 103–116 (1988).

Furst, "Stress Induced Intracellular Glutamine Depletion," Contr. Infusion Ther. Clin, Nutr. vol. 17, pp. 117–136 (1988).

Hubl. et al. "Influence of Molecular Structure and Plasma Hydrolysis on the Metabolism of Glutamine-Containing Dipeptides in Humans," Metab 59 (1989).

Adibi, Siamak A., "Experimental Basis for Use of Peptides as Substrates for Parenteral Nutrition: A Review", Meta. vol. 36, No. 10, 1987 pp. 1001–1011.

Albers, S. et al., "Availability of Amino Acids Supplied by Constant Intravenous Infusion of Synthetic Dipeptides in Healthy Man," Clin. 76 Sci. 643 (1989).

NUTRIENT COMPOSITIONS CONTAINING PEPTIDES AND METHOD FOR ADMINISTERING THE SAME

BACKGROUND OF THE INVENTION

1. Field of the Invention

This invention relates to nutrient compositions for use in clinical nutrition and more particularly, to nutrient compositions containing certain dipeptides.

2. Description of the Prior Art

Proteins are converted to amino acids in the digestive system and the resulting amino acids are used by the body for growth and development. In certain medical situations a patient may be unable to receive proteins. In these situations patients have been given free amino acids. Free amino acids, however, are sometimes not tolerated well by patients and may cause diarrhea and dehydration.

It has been observed that the body can more effectively absorb certain small molecules called dipeptides or tripeptides. In particular, it has been observed that peptides containing the amino acid residue glycine in the N-terminal position are readily assimilable. U.S. Pat. No. 4,340,592 (hereinafter Adibi I). Adibi I requires glycine to be the peptide in the N-terminal position because "glycine-terminated oligopeptides achieve a desirable intact transport of the oligopeptide into a cell. The glycine grouping protects the oligopeptide from hydrolysis into amino acids by the peptidases on a cell membrane . . . The glycine grouping is also lipophilic and the oligopeptide has an enhanced transport through the cell membrane . . . The glycine terminated oligopeptides are particularly water-soluble which permits the use of such oligopeptides in high concentration." Col. 2, ll. 35-55.

It was later found, however, that if glycine-terminated oligopeptides are the only peptide in the nutrient solution, excess glycine may develope.

European Patent Application No. 0,182,356 (hereinafter Adibi II) discloses a nutritional composition containing at least one oligopeptide consisting of a dipeptide or a tripeptide wherein the N-terminal amino acid residue is glycine residue and at least one oligopeptide consisting of a dipeptide or a tripeptide wherein the N-terminal amino acid residue is selected from the class consisting of alanine, lysine and arginine. The oligopeptide concentration is from 0.2 to 30 weight percent. For total parenteral nutrition, the preferred range is from 5 to 15 weight percent of the oligopeptide. The total protein nutrients in the compositions are from 2 to 40 weight percent. These prior teachings suggest the use of amino acids having high solubility in water, such as glycine (25.0 grams/100 ml 25° C.), as the N-terminal amino acid in the oligopeptide.

Adibi et al. conclude that glycine is generally superior to other amino acids as the N-terminal amino acid residue in a dipeptide because a greater fraction of such an intravenously administered dipeptide reaches the tissues. S. Adibi et al., *Influence of Molecular Structure on Half-life and Hydrolysis of Dipeptides in Plasma: Importance of Glycine as N-Terminal Amino Acid Residue*, 35 Metabolism 850, 835 (1986).

Another group that is studying nutrient compositions including dipeptides is Pfrimmer & Co. Two European patents, 0,087,751, hereinafter Pfrimmer I and 0,087,750 (Pfrimmer II) disclose water-soluble peptides. Pfrimmer I discloses a method to parenterally administer low water-soluble amino acids. Two amino acids, tyrosine and cystine, individually have low solubility in water. These amino acids, however, are clinically useful. The disclosed infusion method involves bonding these difficultly soluble amino acids to the two amino groups of the amino acid lysine to produce a tripeptide.

Pfrimmer II discloses the infusion of glutamine as a derivative substituted by α-aminoacyl residues on the α amino group. That is, glutamine is in the "c-terminal" position, in that its alpha amino nitrogen becomes part of the peptide bond with the other amino acid. The preferred dipeptide preparation disclosed in Pfrimmer II is alanyl-glutamine. The aminoacylation of glutamine is reported to achieve a stabilization of the terminal amide group.

Experiments involving the use of total parenteral nutrition containing glycyl-glutamine dipeptides, however, suggest the potential adverse effect of the TPN formulation containing glycyl-glutamine. In this experiment slightly preterm, colostrum-deprived piglets were maintained on total parenteral nutrition from birth to day 7 of life. All piglets in this study have been enrolled and completed the study period in the University of Florida Piglet Neonatal Intensive Care Unit. Ten piglets in the control group received standard neonatal piglet total parenteral nutrition solution containing amino acids, glucose, lipid, vitamins and minerals. Eleven piglets in the experimental group received the same total perenteral nutrition formulation with the exception that 20% of the amino acids in the standard solution was replaced with glutamine. Since the glutamine was in the form of a dipeptide, administration of 1 gram of glutamine required the coadministration of approximately 0.5 gram of glycine. Nine piglets in each group completed the full 7 days of the study. One piglet in the control group and two piglets in the experimental group became septic. The two septic piglets in the experimental group exhibited signs of severe convulsions while the septic piglet in the control group exhibited no signs of convulsions.

To date, the amino acid analyses have been completed on blood samples from six of the piglets in the experimental group and on blood samples from seven of the piglets in the control group. The plasma amino acid data listed below indicate that administration of the glycylglutamine dipeptide increases the plasma glutamine concentrations in the piglets in the experimental group compared to the concentrations measured in plasma from the piglets in the control group.

| PLASMA GLUTAMINE CONCENTRATIONS | | | |
|---|---|---|---|
| CONTROL PIGLETS | | EXPERIMENTAL PIGLETS | |
| Piglet | nmol/ml | Piglet | nmol/ml |
| P253 | 215 | P260 | 709 |
| P259 | 189 | P263 | 805 |
| P262 | 358 | P266 | 646 |
| P265 | 384 | P269 | 415 |
| P268 | 255 | P272 | 272 |
| P271 | 240 | P275 | 417 |
| P274 | 266 | MEAN: | 544 |
| MEAN: | 272 | | |

Based on the problems associated with the above discussed peptides, an alternate method to deliver low water-soluble, and potentially toxic amino acids, such as glutamine, is needed.

SUMMARY OF THE INVENTION

According to the present invention, a nutrient composition comprising an aqueous solution having at least one dipeptide with an N-terminal amino acid selected from the class consisting of glutamine, asparagine, tyrosine, tryptophan, and arginine is provided. Glutamine (4.8 grams/100 mL 30° C.), asparagine (3.5 grams/100 mL at 28° C.), tyrosine (0.45 grams/100 mL 25° C.) and tryptophan (11.4 grams/100 mL 25° C.) and arginine (15.0 grams/100 mL, at 21° C.) are all less soluble in water than glycine (25 grams/100 mL, 25° C.). The C-terminal amino acid is selected from the group consisting of alanine, glycine, tryptopan, arginine, proline and serine. The nutritional solutions contain from about 0.1 to 25.0 percent by weight of oligopeptides, preferably about 0.5 to 5.0 percent by weight. (Arginine solubil: 15.0 grams/100 Ml at 21° C.)

These peptides in a nutrient composition, compared to the administration of equivalent amounts of the free amino acids, will cause a decrease in osmolarity of the solution, will facilitate the administration of amino acids having low water solubility, and will stabilize heat-unstable amino acids such as glutamine, asparagine and tryptophan. The aqueous solution may be suitable for intravenous feeding or for intragastrointestional administration. The aqueous solution itself may contain the other nutrient additives such as fats, glucose, mono- or oligo-saccharides, minerals, trace elements and/or vitamins.

It is an object of this invention to provide a dipeptide having a low water-soluble amino acid in the N-terminal position of the dipeptide, i.e., its carboxyl group partakes in a peptide bond. It is a further object of this invention to provide a dipeptide having stability to sterilization, long-term stability and bioavailability.

DETAILED DESCRIPTION OF THE INVENTION

Aqueous clinical nutrient compositions are prepared which include at least one dipeptide. The dipeptide would be added to enteral or parenteral formulations of either complete or incomplete nutritional content. Each dipeptide has an N-terminal amino acid selected from the group consisting of glutamine, asparagine, tyrosine, tryptophan and arginine. The C-terminal amino acid of the dipeptide is selected from the group consisting of alanine, glycine, proline, tryptophan, arginine and serine.

The concentration of the dipeptide in the aqueous solution is from 0.1 to 25.0 percent by weight. The selection of the particular dipeptide depends upon the requirements for essential and nonessential amino acids. In addition to dipeptides the clinical nutritional solution can contain dextrose, lipid emulsions, vitamins, minerals and trace elements.

Dipeptide additives such as single or multiple entities, as well as a total nutritional formulation which contains dipeptides as one component among many are contemplated by this invention. Dipeptide can be added to enteral or parenteral formulations of either complete or incomplete nutritional content.

In a one liter of amino solution which contains 100 grams of amino acids plus dipeptides, each of the dipeptides is present as shown in Table 1.

TABLE 1

| Dipeptide | One Liter Solution Grams |
|---|---|
| glutaminyl-glycine | 0.1–25.0 grams |
| glutaminyl-alanine | 0.1–25.0 grams |
| glutaminyl-arginine | 0.1–25.0 grams |
| gluatminyl-proline | 0.1–25.0 grams |
| Tyrosyl-glycine | 0.1–8.0 grams |
| Tyrosyl-alanine | 0.1–8.0 grams |
| Tyrosyl-proline | 0.1–8.0 grams |
| arginyl-tyrosine | 0.1–8.0 grams |

The structural formula of a glutaminyl-glycine dipeptide is as follows:

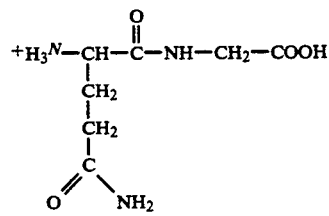

The glutamine unit:

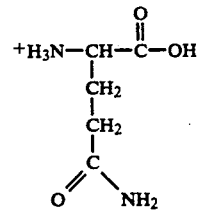

supplies the N-terminal group in the glutaminyl-glycine dipeptide described above. Similarly, tyrosine and arginine function as the N-terminal amino acid in the dipeptides.

METHOD OF ADMINISTRATION

The aqueous oligopeptide may be ingested orally along with other nutrients such as conventional foods of prepared vitamins, fats, glucose or other mono-saccharides, oligosaccharides, minerals and trace elements. For parenteral administration, a supply of the oligopeptide solution may be merged through a Y-connection with a supply of glucose solution or other parenteral solutions. The oligopeptide solutions may be mixed with glucose solutions and/or other parenteral solutions to create a mixture which may be administered parenterally.

The administration of oligopeptides rather than free amino acids allows administration of the same amount of amino acid residue in solutions which are less hypertonic and therefore can be introduced into peripheral veins, which is not considered to be a surgical procedure.

Although the invention has been shown in connection with certain specific embodiments, it will be readily apparent to those skilled in the art that various changes in form and arrangement of steps can be made to quit requirements without departing from the spirit and scope of the invention.

We claim:
1. A nutrient composition comprising an aqueous solution including glutaminyl-glycine.

2. The nutrient composition of claim 1 further comprising another nutrient selected from the class consisting of lipid emulsion, glucose, oligosaccharides, minerals, trace elements and vitamins.

3. A nutrient composition comprising an aqueous solution of free amino acids and glutaminyl-glycine, said glutaminyl-glycine comprising from 0.1 to 25.0 percent by weight of said composition.

4. A method of administering a nutrient composition to a patient which comprises orally administering to said patient an aqueous solution of claim 1.

5. A method of administering a nutrient composition to a patient which comprises parenterally administering to said patient an aqueous solution of glutaminyl-glycine.

6. A method of administering a nutrient composition to a patient which comprises orally administering to said patient an aqueous solution of claim 3.

7. A method of administering a nutrient composition to a patient which comprises parenterally administering to said patient an aqueous solution including 0.1 to 25 percent by weight of glutaminyl-glycine.

* * * * *